(12) United States Patent
Pagnon

(10) Patent No.: US 10,046,557 B2
(45) Date of Patent: Aug. 14, 2018

(54) DEVICE FOR MEASURING FLOW RATE AND VISCOSITY AND USE THEREOF IN A PRINTER

(71) Applicant: Dover Europe Sàrl, Vernier (CH)

(72) Inventor: Alain Pagnon, Bourg les Valence (FR)

(73) Assignee: Dover Europe Sàrl, Vernier (CH)

( * ) Notice: Subject to any disclaimer, the term of this patent is extended or adjusted under 35 U.S.C. 154(b) by 0 days.

(21) Appl. No.: 15/465,869

(22) Filed: Mar. 22, 2017

(65) Prior Publication Data
US 2017/0274641 A1   Sep. 28, 2017

(30) Foreign Application Priority Data

Mar. 22, 2016   (FR) ...................................... 16 52440

(51) Int. Cl.
*B41J 2/175*   (2006.01)
*B41J 2/03*   (2006.01)
(Continued)

(52) U.S. Cl.
CPC ................. *B41J 2/03* (2013.01); *B41J 2/175* (2013.01); *B41J 2/195* (2013.01); *G01F 1/34* (2013.01); *G01N 11/08* (2013.01)

(58) Field of Classification Search
CPC .......... B01J 2219/00378; B01L 3/0268; B01L 3/0265; B01L 2400/0487; G01N 2035/1041; G01N 9/32; B01N 11/08
See application file for complete search history.

(56) References Cited

U.S. PATENT DOCUMENTS 4,600,928 A * 7/1986 Braun .................. B41J 2/16552
    347/27
4,641,535 A   2/1987 Malguarnera
(Continued)

FOREIGN PATENT DOCUMENTS

DE   10 2005 024 575 A1   12/2006
EP       3 123 523         10/1984
(Continued)

OTHER PUBLICATIONS

M.A. Boillat et al., "A Differential Pressure Liquid Flow Sensor for Flow Regulation and Dosing Systems" IEEE, 1991.
(Continued)

*Primary Examiner* — John P Zimmermann
(74) *Attorney, Agent, or Firm* — Pearne & Gordon LLP

(57) ABSTRACT

A device (20) for measuring the flow rate and the viscosity of ink sent to a print head (50) of an ink jet printer, comprising: a conduit (200), for supplying the print head (50), this conduit being provided with a $1^{st}$ pressure (Pin) sensor (26) at a first end and a $2^{nd}$ pressure (PHead) sensor (56) at a $2^{nd}$ end, circuit or controller (26, 56) for measuring at least the pressure (PHead) of the $2^{nd}$ pressure sensor (56) and the pressure difference (Pin–PHead) between the $1^{st}$ pressure sensor (26) and the $2^{nd}$ pressure sensor (56).

20 Claims, 5 Drawing Sheets

(51) Int. Cl.
  *B41J 2/195* (2006.01)
  *G01F 1/34* (2006.01)
  *G01N 11/08* (2006.01)

(56) References Cited

U.S. PATENT DOCUMENTS

| | | | | |
|---|---|---|---|---|
| 4,905,503 | A * | 3/1990 | Langrick | B41J 2/195 73/54.06 |
| 5,747,674 | A * | 5/1998 | Moracchini | G01N 25/00 73/152.18 |
| 5,927,547 | A * | 7/1999 | Papen | B01L 3/0268 222/333 |
| 6,537,817 | B1 * | 3/2003 | Papen | B01L 3/0268 134/22.11 |
| 7,192,121 | B2 | 3/2007 | Barbet | |
| 8,540,350 | B2 | 9/2013 | Barbet | |
| 9,844,936 | B2 * | 12/2017 | Barbet | B41J 2/14008 |
| 2009/0032064 | A1 * | 2/2009 | Gifford | B08B 3/044 134/18 |
| 2016/0347074 | A1 | 12/2016 | Ribeiro et al. | |

FOREIGN PATENT DOCUMENTS

| | | |
|---|---|---|
| EP | 3 287 372 A1 | 10/1988 |
| EP | 3 329 354 | 8/1989 |
| EP | 2 075 552 A2 | 7/2009 |
| FR | 2 851 495 A1 | 8/2004 |
| FR | 2 952 851 A1 | 5/2011 |
| GB | 1 408 657 | 10/1975 |
| JP | 554-021723 A | 2/1979 |
| JP | H09-201980 A | 8/1997 |
| NO | 31/28701 A1 | 4/2001 |

OTHER PUBLICATIONS

French Search Report issued in French Patent Application No. FR 1652440 dated Nov. 30, 2016.
French Search Report issued in French Patent Application No. FR 1652439 dated Dec. 16, 2016.
Extended European Search Report issued in Patent Application No. EP 17 16 2439 dated Jun. 19, 2017.
French Search Report issued in French Patent Application No. FR 1657863 dated Dec. 16, 2016.
Extended European Search Report issued in Patent Application No. EP 17 16 2436 dated Jun. 26, 2017.

\* cited by examiner

DEVICE FOR MEASURING FLOW RATE AND VISCOSITY AND USE THEREOF IN A PRINTER

TECHNICAL FIELD AND PRIOR ART

The invention relates to continuous ink jet printers, in particular but not exclusively binary continuous ink jet printers provided with a multi-nozzle drop generator. It targets in particular an improvement to a circuit for supplying and recovering ink and solvent of these printers.

Continuous ink jet printers include:
an ink drop generator,
means for separating the trajectories of the drops produced by the generator and directing them to a printing support or to a recovery gutter.

In FIG. 1 is represented the main units of an ink jet printer. The printer comprises a console 300, a compartment 400 containing notably circuits for conditioning ink and solvents, as well as reservoirs for ink and solvents. Generally the compartment 400 is in the lower part of the console. The upper part of the console comprises the command and control electronics as well as visualisation means. The console is hydraulically and electrically connected to a print head 100 via an umbilical 200. A gantry, not represented, makes it possible to install the print head facing a printing support 800.

The printing support 800 moves along a direction materialised by an arrow. This direction is perpendicular to an alignment axis of the nozzles.

The drop generator includes nozzles aligned on a nozzle plate along an X axis of alignment of the nozzles. During printing, jets of ink are ejected in a continuous manner by these nozzles in a direction Z perpendicular to the nozzle plate. Among continuous ink jet printers may be distinguished deviated continuous ink jet printers and binary continuous ink jet printers. In multi-deflection deviated continuous ink jet printers, the drops formed from a nozzle during printing of a position of a printing support are deflected or non-deflected. For each printing position and for each nozzle, a segment perpendicular to the direction of movement of the printing support is printed. The deflected drops are deflected in such a way that they are going to strike the printing support on the part of the printed segment that has to be printed taking account of the pattern to print. Non-deflected drops are recovered by a recovery gutter. Deviated continuous ink jet printers in general comprise few injection nozzles, but each nozzle can print, for each printing position of the support, several pixels spread out on the printing segment as a function of the pattern to print.

In binary continuous ink jet printers, ink coming from a nozzle only prints one pixel per printing position. The pixel considered does not receive any drop or receives one or more drops, as a function of the pattern to print. Hence, for good printing rapidity, the nozzle plate comprises a large number of nozzles, for example 64, enabling the simultaneous printing of as many pixels as nozzles. Drops not intended for printing are recovered by a recovery gutter. Such printers and print heads with continuous jets have been widely documented.

A general structure of print head for a binary continuous ink jet printer is explained below, in relation with FIG. 2.

The head represented includes a drop generator 11. On a nozzle plate 2 are aligned, along an X axis, a whole number n of nozzles 4, of which a first 4₁ and a last nozzle 4ₙ.

The first and last nozzles (4₁, 4n) are the nozzles the furthest away from each other.

Each nozzle has an axis of emission of a jet parallel to a direction or a Z axis (situated in the plane of FIG. 2), perpendicular to the nozzle plate and to the X axis mentioned previously. A third axis, Y, is perpendicular to each of the two axes X and Z, the two axes X and Z extending in the plane of FIG. 2.

Each nozzle is in hydraulic communication with a pressurised stimulation chamber. The drop generator comprises as many stimulation chambers as nozzles. Each chamber is equipped with an actuator, for example a piezoelectric crystal, the command of which makes it possible to cut the continuous jet of ink into drops or sections. An example of design of a stimulation chamber is described in the document U.S. Pat. No. 7,192,121.

Downstream of the nozzle plate are located means, or sorting unit, 6 which make it possible to separate drops intended for printing from drops or sections of jets that do not serve for printing. In FIG. 2 is represented a trajectory a of drops of ink passing through a slot 17 (represented in broken lines in FIG. 2), and a trajectory b of drops of ink directed to a recovery gutter 7. The slot is open on the outside of the cavity and enables drops of ink intended for printing to get out; it is parallel to the direction X of alignment of the nozzles, the axes of direction Z of the nozzles passing through this slot, which is located on the face opposite to the nozzle plate 2. The slot and the gutter have, in the direction X, a length at least equal to the distance between the first and last nozzle.

The drops emitted or sections of jets, emitted by a nozzle and intended for printing, follow a trajectory a along the Z axis of the nozzle, then are going to strike a printing support 800, after having passed via the outlet slot 17.

The drops emitted, or sections of jets emitted, by a nozzle and not intended for printing are deviated by the means 6 (they follow a trajectory such as the trajectory b) and are recovered by the recovery gutter 7 then recycled.

Reference could be made, notably with regard to the formation of the jets and their break up to form drops, as well as with regard to the deflection of the drops, for example to the document U.S. Pat. No. 8,540,350 (FR 2 952 851) which describes a method for avoiding crosstalk between jets coming from nozzles adjacent to each other.

Reference could also be made to the prior art described in the U.S. Pat. No. 7,192,121 (FR 2851495) relative to the jet break up positions depending on whether a drop formed by the break up of the jet is intended or not to strike the printing support.

For single jet printers, knowledge of the jet speed (obtained with a dedicated means) suffices to assure the control of the pressure. In fact, the pressure of the circuit is controlled so as to obtain and maintain the target jet speed.

For a twin jet CIJ printer, knowledge of the speed of the two jets is generally used to ensure the control of the pressure of the circuit. The average of the speeds of the two jets is often chosen as the target speed to reach.

For a printer with n-jets (n of the order of 32, 64, 128 or more) the principle of controlling with the average of the jet speeds is only applicable if dedicated costly and complex means are implemented to measure the individual speed of the jets.

The problem is thus posed, in particular in a printer with n-jets (n≥2), of finding a simple to implement device, which makes it possible to obtain the speed of the different jets.

Furthermore, another problem is that of the measurement of the viscosity of an ink used during printing operations using an ink jet printer, in particular of multi-jet type.

Viscosity is a parameter of the ink, of which potential variations may affect printing quality.

The problem is thus posed, notably in a printer with n-jets (n≥2), of finding a device that is simple to implement, which make it possible to obtain the viscosity of the ink.

Preferably such a device and/or method are adaptable to a CIJ type printer, with a single jet.

BRIEF DESCRIPTION OF THE INVENTION

The present invention firstly relates to a device for measuring the flow rate and the viscosity of ink sent to a print head, for example multi-jet, of an ink jet printer, comprising:
- a conduit, for supplying said print head, this conduit being provided with a $1^{st}$ pressure (Pin) sensor at a first end and of said conduit a $2^{nd}$ pressure (PHead) sensor at a $2^{nd}$ end of said conduit or in said print head,
- means for measuring at least the pressure (PHead) of the $2^{nd}$ pressure sensor and the pressure difference (Pin−PHead) between the $1^{st}$ pressure sensor and the $2^{nd}$ pressure sensor.

A flow meter according to the invention makes it possible to measure in an overall manner the flow rate of all the jets of a multi-jet print head and is particularly suited when the individual speed of each jet is not known. It makes it possible in fact to then obtain a measurement of the average speed of the jets.

It is moreover suited to a CIJ type head, with a single jet.

In fact, the nozzles of the printers preferably have identical, or similar, geometric characteristics.

This geometric similarity of the nozzles makes it possible to merge speed and flow rate for several nozzles outputting in parallel (as is the case in a multi-jet printer). The error associated with the fact of merging the averages of the speeds of the jets and total flow rate of all the jets is very small and in keeping with the expected quality of the control or servo-control (with a precision that is for example equal to 2%).

Such a device may further comprise means for calculating the flow rate and the viscosity of the ink as a function of the pressure (PHead) of the $2^{nd}$ pressure sensor and the pressure difference (Pin−PHead).

According to one embodiment, the means for calculating the flow rate of the ink and the viscosity are capable of calculating them as a function of the hydraulic characteristics (αHead, βHead) of the print head, the regular head loss coefficient ($β_0$) of said conduit, the specific gravity or volumetric mass density (p) (also called density, in kg/m³ for example) of the ink, the pressure difference (Pin−PHead) and the pressure (Pin).

Such a device may comprise means for correcting, preferably as a function of temperature, a measurement difference, for at least one same pressure, between the $1^{st}$ pressure sensor and the $2^{nd}$ pressure sensor and/or a sensitivity error of at least one of the pressure measurement devices.

Such a device may comprise means for correcting, preferably as a function of temperature, a measurement difference, for at least one pressure, between a pressure value measured by the $2^{nd}$ pressure sensor and said actual pressure.

The $2^{nd}$ pressure sensor is advantageously arranged in said print head.

The present invention also relates to a circuit for supplying with ink and/or with solvent an ink jet printer comprising a device for measuring the flow rate and the viscosity of ink according to the present invention, and means for controlling or servo-controlling or correcting the pressure and/or the viscosity of the ink supplied as a function of the measurements of the flow rate and the viscosity of the ink.

The present invention also relates to an ink jet printer comprising:
- a print head,
- means for forming a flow of fluid to send to said print head,
- a device for measuring the flow rate and the viscosity of ink sent to said print head, according to the invention.

The present invention also relates to a printing method using an ink jet printer, comprising a measurement of the flow rate and/or the viscosity of ink using a device according to the invention.

Such a printing method may further comprise a step of measuring the flow rate and/or the viscosity of ink and a step of correcting the flow rate and/or the viscosity of ink.

BRIEF DESCRIPTION OF THE DRAWINGS

Other advantages of the invention will become clear at the same time as details will be given in an exemplary embodiment of the invention which will now be described with reference to the appended drawings in which.

DETAILED DESCRIPTION OF EMBODIMENTS

Figure 3:
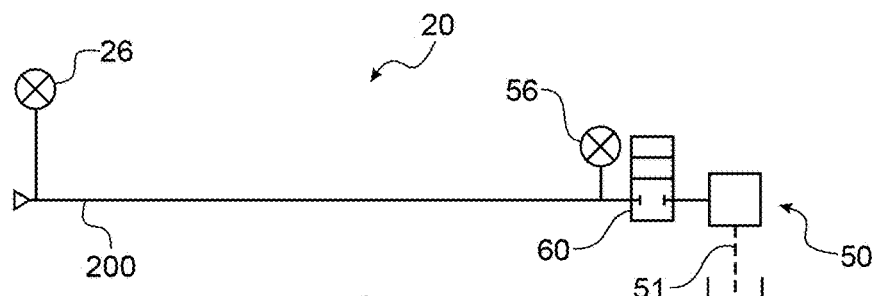
FIG. 3 is an exemplary embodiment of a device according to the invention, applied to a circuit for supplying a print head of an ink jet printer with ink.

An example of a device 20 according to the invention is represented in FIG. 3.

Figure 2:
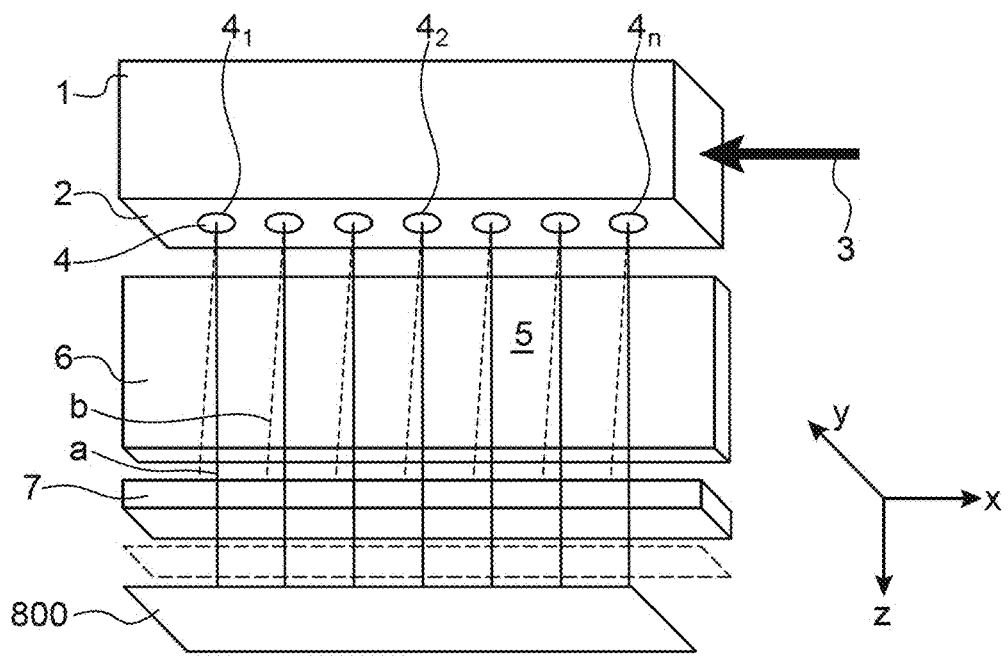
FIG. 2 represents a schematic cavalier view of a print head mainly revealing the components of the print head situated downstream of the nozzles.

It comprises a pressure sensor 26 (or $1^{st}$ pressure sensor), preferably a flush membrane pressure sensor (which has reduced dead volume), arranged so as to measure the pressure of ink that flows in the line for supplying the print head, for example in the supply conduit (or pipe), also called umbilical, 200, the outlet of which is connected to a multi-jet print head 50 (which produces jets of ink 51). The structure of this head is for example of the type described above in relation with FIG. 2. In a variant the print head is single jet.

In a flush membrane pressure sensor, the pressure sensitive element is a flat membrane situated at one end of the sensor, which avoids any retention of fluid or material; thus, the membrane is flush with the measured flow. This avoids the presence of a cavity, above the diaphragm, which could collect fluid material from the measured flow which, in certain applications, may be very undesirable. The invention makes it possible to use a pressure sensor with non-flush membrane; but the presence of a cavity, often synonymous with dead volume, degrades the operation of the assembly, notably on account of the steps of purging and cleaning implemented to use this type of sensor.

The umbilical 200 has a certain flexibility, so as to be able to bring the print head to various positions. It is most often made of PTFE. The umbilical has for example a length comprised between 2 m and 8 m. The inner diameter of the pipe in which the fluid flows varies very little over its length, it is for example comprised between 1.5 mm and 3 mm.

At the inlet and at the outlet of the umbilical may be arranged fittings, respectively inlet and outlet. The passage diameters of these fittings are close to the inner diameter of the pipe 200. It is possible to ignore the head loss of the fittings in view of the head loss spread out over the whole length of the pipe 200. This hypothesis has been verified during tests.

A coefficient βo expresses the hydraulic characteristic of the umbilical; in fact singular head losses (in the fittings) are negligible.

An electromagnetic valve 60 with two orifices (inlet and outlet) and two positions (open or closed) enables the passage (or stoppage) of fluid to the print head. This electromagnetic valve is located in the print head, near to the ink ejection nozzles.

A pressure sensor 56 (or $2^{nd}$ pressure sensor) is situated upstream of the head (for example at the outlet of the umbilical 200), or in the head, just upstream of the electromagnetic valve 60; this sensor makes it possible to provide a measurement of the operating pressure of the ink in the head. Once again, it is, preferably, a flush membrane sensor.

A dedicated temperature sensor (not represented) may moreover be provided, which makes it possible to measure the temperature T of the fluid. But pressure sensors 56 that integrate temperature measurement exist, which enable, for reduced cost, knowledge of T.

The hydraulic circuit of the head comprises conduits for supplying the set of nozzles (which are calibrated orifices of small dimension through which the jets of ink come out). Coefficients (αHead, βHead) express the hydraulic characteristics of this circuit.

The sensor 26 measures a pressure designated Pin, the sensor 56 measures a pressure designated PHead. The umbilical 200 is arranged between the 2 pressure sensors 26, 56.

The relative position of the pressure sensors 26, 56 is not a parameter of the system to take into account provided that this position does not change between the start-up of the printer (for example at the moment of the establishment of the offset, as explained below) and during operation.

If this relative position changes during the operation of the printer, then a non-acceptable error may result therefrom. The monitoring of (Pin–P Head) with detection of a very rapid non-justified variation (for example: a relative variation of more than 5% of the operating pressure Pin between 2 consecutive measurement points) by the physically possible change in the conditions (flow rate and viscosity) makes it possible to warn of an abnormal situation. For example, an intervention by the operator then makes it possible to instruct the system on the new difference of altitude value between the two sensors. In fact, the value of Pin-P Head, at zero flow rate, takes account, among other things, of the difference in height between the head and the ink circuit (thus between the 2 sensors 26, 56).

It may be sought to compensate "offset" errors, that is to say on the one hand of the umbilical 200 and on the other hand of the sensor 56.

When the ink circuit is not pressurised, the sensor 56 can measure a pressure, which can have various origins (orientation of the head, and/or static errors of the sensor, etc.). A compensation of this "offset" (or measurement difference compared to the measured real pressure) may be carried out in different ways.

According to a $1^{st}$ method, a compensation is carried out at zero flow rate by opening the valve 60. Thus, without pressurising the circuit, the valve 60 is opened. The pressure sensor 56 sees the relative static pressure of the fluid (because a relative sensor measures pressure compared to atmospheric pressure). The value announced by the measuring chain constitutes the sought after "offset" and is going to be able to be used for any other measurement, which will thus be referenced at this offset measurement (Pressure to take into account=Measured pressure−Offset). This information may be stored in a memory associated with the sensor 56.

The static pressure of the fluid is thus compensated, which is the parasitic pressure generated by the column of fluid corresponding to the difference in height between the head and the ink circuit (or, preferentially, the pressure sensor 26).

Conversely, the opening of the valve 60 may cause an entry of air (if the head is situated at an altitude above the ink circuit) or lead to a low running (or spillage) of ink (if the head is situated at an altitude lower than that of the ink circuit). The error on the measurement of the offset, associated with the fact that the flow rate of fluid (linked to these runs or spillages) is not strictly zero (the measured pressure is then not perfectly static), is small, but there is a risk on the quality (directivity of the jets, establishment speed) of ink start-ups of the jets (on account of air inflows and/or runs or spillages).

According to a $2^{nd}$ method, complete knowledge of the main characteristics of the sensor is employed; at least the following are used:

a) the "offset" value at a given temperature: Offset (T0).

b) the offset drift as a function of temperature: dOffset.

These items of information may for example be obtained from the supplier of the sensor (who carries out an individual characterisation in air of each sensor) and may be stored in a memory associated with the sensor 56.

The compensation is carried out in the following manner:

$$\text{Offset}(T)=\text{Offset}(T0)+d\text{Offset}(T-T0)$$

as soon as the temperature T is known.

This temperature (T) may be obtained thanks to a dedicated sensor, or as already indicated above, by a pressure sensor 56 which integrates a temperature measurement.

The advantages of this $2^{nd}$ method are, on the one hand, its ease of implementation associated with the fact that the compensation takes place by calculation (no specific sequence implementing components is necessary, thus the offset is calculated without any hydraulic perturbation of the circuit) and, on the other hand, the compensation can take place at any temperature.

But knowledge of the characteristics of the sensors may involve an extra cost. It may also be noted that the static pressure of the fluid is not compensated because the characteristic values are established in air and the position of the head influences this static pressure. Nevertheless, the error generated by the position of the head (several mbars over the measured operating pressure) does not affect in a significant manner the expected precision. Finally, this compensation does not integrate errors (which may be very small, notably if an analogue-digital converter of at least 12 bits is used) associated with the measuring chain.

According to a $3^{rd}$ method, partial knowledge of the characteristics of the sensor is employed.

It is a variant of the $2^{nd}$ method, for which the offset at a given temperature is known, by a simple and inexpensive sequence carried out, for example, during the production of the machine. In fact, the circuit is then still in air; the pressure announced by the measuring chain is thus measured, this value constitutes the "offset" that will be applied to all later pressure measurements. Once again, this information may be stored in a memory associated with the sensor 56.

The advantages of this variant are its ease of implementation, associated with the fact that the compensation takes place through calculation (no sequence implementing components is necessary). And the measured "offset" value" is indeed representative if the operating temperature is close to the temperature at which it has been measured.

Measuring chain errors (very small) are very well compensated at a temperature close to the temperature at which the offset was measured during the production of the machine.

The flaws of this principle are the following:
the problem of offset temperature drift may be posed. It may thus be necessary to verify the drift values to ensure that the error generated does not affect in a significant manner the measurement precision,
it may also be noted that the static pressure of the fluid is not compensated because the characteristic values were established in air and the position of the head influences this static pressure. Nevertheless, the error generated (several mbars over the measured operating pressure) does not affect in a significant manner the expected precision; indeed the typical error is 3 mbars, for an operating pressure greater than 3 bars, which represents a typical error below one thousandths (1/1000).

According to a $4^{th}$ method, a compensation of the generalised offset is carried out ("offset" at the operating pressure). It is a variant of the $2^{nd}$ method, for which the characteristics of the sensor are known, making it possible to compensate fully errors associated with the sensor and with temperature variations.

This $4^{th}$ method makes use, at least, of the following four items of information concerning the characteristics of the pressure sensor with respect to its offset and to its sensitivity:

Offset at a given temperature $T_0$: Offset $(T_0)$.
Offset drift as a function of temperature: d Offset.
Sensitivity at a given temperature $T_0$: $S(T_0)$.
Sensitivity drift with temperature: dS.

These items of information may be obtained from the supplier of the sensor and may be stored in a memory associated with the sensor 56.

The relation making it possible to know the pressure (P) as a function of the measurement (Mesure) and of the temperature (T) is then:

$$P = \frac{\text{Mesure}}{S(T0) + dS*(T-T0)} - (\text{Offset}(T0) + d\,\text{Offset}(T-T0))$$

As regards the umbilical 200, an "offset" error may stem from measurement differences between the two sensors 26 and 56, which do not measure the same value at zero flow rate, while the pressure is the same at the inlet and at the outlet of the umbilical, or at the 2 points where these sensors measure the pressures.

As explained below, one or several treatment(s) may be carried out with a view to the compensation of this "offset" (that is to say measurement differences between the two sensors 26 and 56). This is easier to carry out if these 2 sensors are identical than if they are different; in fact, the pressure differential is considered, which is easy to calculate when the sensors are identical (they have in fact the same sensitivity); if the sensors are different, they do not have the same sensitivity, the calculation is less direct but feasible.

According to a $1^{st}$ method, a compensation is carried out at zero flow rate (the pump for pressurising the ink is stopped and the valve 60 is closed).

Before the start-up of the ink circuit (and thus at zero flow rate) the measured values of Pin and P Head are recorded. The difference in these values (Pin–P Head) constitutes the offset to apply to future measurements and may be stored, for this purpose, in a memory of the system.

The advantages of this principle are its ease of implementation associated with the fact that the compensation takes place by calculation (no sequence implementing components is necessary). The compensation is simple, without influence of the hydraulic circuit (stopped during the sequence).

Moreover, this offset measurement automatically integrates the difference in height between the altitude of the sensor 26 and that of the sensor 56.

The flaws of this principle are the following:
the compensation takes place at the start-up temperature: if the temperature changes during operation there is no correction for temperature drift,
the compensation integrates the difference in height in the start-up conditions of the printer. If the difference in height changes, which happens when the head is located firstly on the start-up station then on the working position (on the conveyor) when the printer is ready to print, then neither the measurement nor the compensation of offset obtained in this way can be used,
the compensation does not integrate sensitivity errors (difference in sensitivity between the 2 sensors 26 and 56).

According to a $2^{nd}$ method, a compensation with pressure is carried out, but without flow rate.

After the start-up of the ink circuit (thus under pressure) and before the start-up of the jets (and thus at zero flow rate in the umbilical) the measured values of the sensors 26 and 56 are recorded. The difference between the measured values (Pin–P Head) constitutes the offset to apply to future measurements. In order to increase the precision of the system, the pressure may be regulated on the basis of the future operating pressure (calculable by the machine). These values may be stored in a memory associated with the sensors 26, 56.

The advantages linked to this principle are the following:
the offset automatically integrates the difference in height between the altitude of the sensors 26 and 56,
the compensation integrates the effects of the offset (value of the measuring chain for a zero pressure) but also sensitivity errors (hence the interest of carrying out the compensation at the future operating pressure to optimise the precision).

The flaws of this principle are the following:
the compensation takes place at the start-up temperature; if the temperature changes during operation, there is no correction for temperature drift,
the compensation integrates the difference in height in the start-up conditions of the printer. If the difference in height changes, which happens when the head is located firstly on the start-up station, then on the working position (on the conveyer) when the printer is ready to print, then the measurement and the compensation of offset obtained in this way cannot be used.

How the flow rate and the viscosity may be measured will now be described in greater detail using the system described above in relation with FIG. 3.

These measurements may notably result from knowledge of the following parameters:
- the hydraulic characteristics of the print head; more exactly the two coefficients αHead and βHead characteristic of the singular and regular head losses of the head,
- the hydraulic characteristics of the umbilical 200, more exactly the coefficient βo characteristic of the regular head losses,
- the physical characteristics of the fluid (ink), in fact the specific gravity (or density or volumetric mass density) and the viscosity of the fluid,
- the pressure difference between the inlet pressure (Pin) and the outlet pressure (PHead) of the umbilical 200,
- the operating pressure PHead measured by the sensor 56.

Potentially, it is possible to take account of the offset, which stems from measurement differences between the sensors 26, 56, of the umbilical 200, and which may be measured as already explained above.

Potentially, it is possible to take account of the offset of the sensor 56, the operating pressure PHead then being corrected for this offset, measured as already explained above.

The equations that model a system such as that described above, notably that of FIG. 3, are the following:

$$(\text{Pin}-P\text{Head})m-(\text{Pin}-P\text{Head})\text{Offset}=\beta_0 \cdot \mu \cdot q \qquad (1)$$

$$(P\text{Head})m-(P\text{Head})\text{Offset}=\alpha\text{Head} \cdot \rho \cdot q^2+\beta\text{Head} \cdot \mu \cdot q, \qquad (2)$$

in which:
- (Pin–P Head)m is the pressure difference measured between the inlet and the outlet of the umbilical 200 when the flow rate has the value q,
- (Pin–P Head)Offset is the pressure difference measured between the inlet and the outlet of the umbilical 200 at zero flow rate,
- (P Head)m is the operating pressure measured in, or near to, the print head (with the sensor 56) when the flow rate has the value q,
- (P Head)Offset is the operating pressure measured in, or near to, the print head at zero flow rate.

Hereafter, and in order to simplify the presentation, the following notations will be used:
- Pin–PHead instead of (Pin–P Head)m–(Pin–P Head)Offset,
- P Head instead of (PHead)m–(P Head)Offset.

The equations are then written:

$$(\text{Pin}-P\text{Head})=\beta_0 \cdot \mu \cdot q \qquad (1')$$

$$(P\text{Head})=\alpha\text{Head} \cdot \rho \cdot q^2+\beta\text{Head} \cdot \mu \cdot q, \qquad (2')$$

Finally:
- ρ is the specific gravity (or density, for example in kg/m³) of the fluid,
- q is the flow rate traversing the system,
- μ is the dynamic viscosity of the fluid.

The conventional resolution of these two equations with two unknowns (flow rate and viscosity) gives the following result:

$$q = \sqrt{\frac{(P\text{ Head} - (\text{Pin} - P\text{ Head}) * \beta\text{ Head}/\beta\text{umbilical})}{(\alpha\text{ Head} * \rho)}}$$

And $$\mu = \frac{(\text{Pin} - P\text{ Head})}{(\beta\text{umbilical})} \bigg/ \sqrt{\frac{(P\text{ Head} - (\text{Pin} - P\text{ Head}) * \beta\text{ Head}/\beta\text{umbilical})}{(\alpha\text{ Head} * \rho)}}$$

Aspects concerning knowledge of the different parameters of these relations are discussed below.

As regards the operating pressure PHead, it is obtained by acquisition of the signal delivered by the pressure sensor 56. The gross value delivered by the sensor may moreover be corrected for offset, as explained above.

The measuring chain may be equipped with a high performance converter, better than 12 Bits, preferably a 16 Bit converter.

As regards the measurement of Pin–PHead, it is carried out while integrating, preferably, the offset as already explained above.

The measuring chain may be equipped with a high performance converter, better than 12 Bits, preferably a 16 Bit converter. For example, for a measurement of Pin–PHead of the order of 100 mbars, the resolution error, in %, having for origin a 16 Bit converter is limited to 0.15%.

As regards the determination of the hydraulic characteristic parameter $\beta_0$, the following operating equation may be used:

$$\text{Pin}-P\text{Head}=\beta_0 \times \mu \times q$$

where Pin–PHead is the pressure difference between the inlet and the outlet of the umbilical (this value is known by measurement).

It may be observed that Pin–P Head is a linear function of q, it is thus advantageously possible to plot Pin–P Head as a function of q. The slope of the line obtained is $\beta_0 \times \mu$, knowledge of μ by measurement in the laboratory (for example) enables $\beta_0$ to be obtained.

2 points with separate flow rates may suffice to determine $\beta_0$, nevertheless the curve may advantageously be plotted with several flow rate values.

Knowledge of several points advantageously enables the use of a linear regression, which makes it possible to:
a) verify that the intercept is close to 0 and that the offset is thus well compensated,
b) obtain the value of $\beta_0$ by dividing the slope by the known value, or measured in the laboratory, of the viscosity.

In addition, it is possible to use the correlation coefficient to assess the quality of the adjustment. It has been verified, by tests, that the correlation coefficient of the regression is really close to 1 (a value greater than 0.99 was obtained by tests).

As regards the determination of the hydraulic characteristics αHead and βHead, it is possible to use the following operating equation:

$$P\text{Head}=\alpha\text{Head} \cdot \rho \cdot q^2+\beta\text{Head} \cdot \mu \cdot q$$

where P Head is the pressure value (potentially corrected for offset) delivered by the sensor 56.

By observing that by dividing the two terms of the equation by the flow rate q, the equation becomes linear, it is seen that PHead/q may advantageously be plotted as a function of q.

2 points with separate flow rates may suffice to determine the coefficients, nevertheless the curve may advantageously be plotted with several flow rate values around the nominal flow rate.

Knowledge of several points advantageously enables the use of a linear regression that makes it possible to determine:

a) βHead·μ, from the intercept, and thus βHead, by dividing this intercept by the known value (or measured in the laboratory) of the viscosity μ, b) The slope of the line, i.e. αHead·ρ; by dividing this value by ρ, the coefficient αHead is obtained.

In addition, it is possible to use the correlation coefficient (absolute value close to 1) to assess the quality of the adjustment. A value greater than 0.99 has been obtained by tests.

As regards the characteristic ρ (specific gravity or density, for example in kg/m$^3$) of the ink, for a given fluid the value of this characteristic may be measured experimentally and for example given in the form of a table of values or graph, which can be memorised and supply data useful during the calculation.

Figure 4:
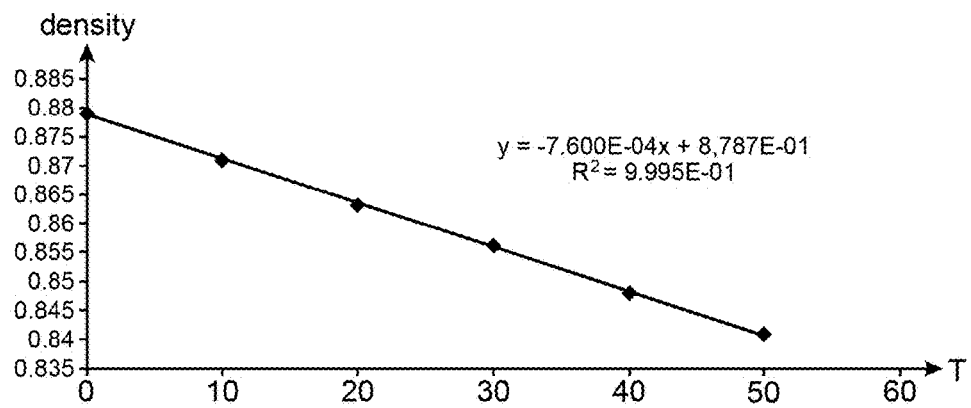
FIG. 4 illustrates the change in the density of an ink as a function of temperature.

The example of FIG. 4 is relative to an ink and gives in graphic form the density (the values given by this figure may be multiplied by 1000 to have the value of ρ in legal units).

For a temperature of 20° C. the specific gravity is 863 kg/m$^3$.

It may be seen in this example that the density of the ink changes in a decreasing but slight manner over the range of temperatures considered (for example between 0° and 50° C.). Preferably, it would be necessary to know the real value of the specific gravity which takes account of the fact that the ink is not necessarily in its nominal conditions (by evaporation or dilution effect). Nevertheless, the error made is very limited and is acceptable with the precision required for the provided application and/or the control of an ink jet printer.

Figure 1:
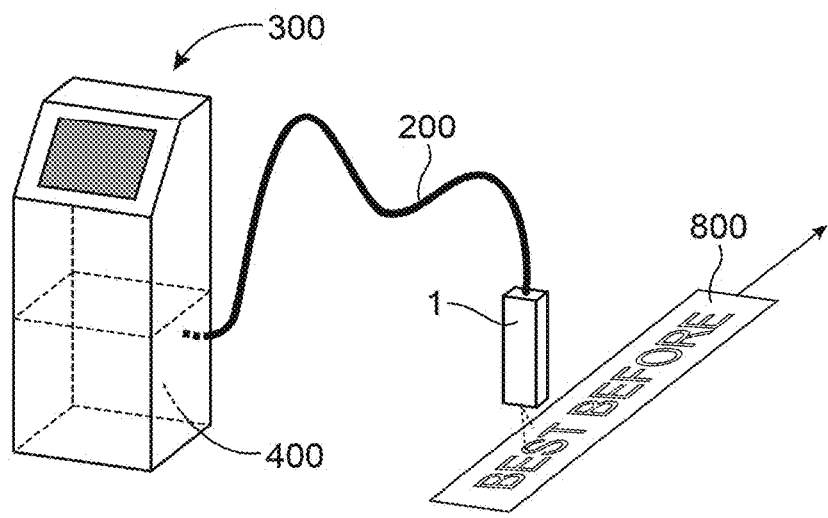
FIG. 1 is a perspective view of an ink jet printer known from the prior art.

A flow meter and/or a head according to the invention may be implemented in a printer such as that described above in relation with FIG. 1. This comprises notably a print head 1 (or 50: FIG. 3)), generally offset with respect to the body of the printer 300, and connected thereto by means, for example in the form of a flexible umbilical 200, grouping together the hydraulic and electrical connections enabling the operation of the head. The umbilical 200 may incorporate the pressure sensors 26, 56 as explained above (see FIG. 3).

The body 300 comprises means forming controller or control means.

The latter comprise for example a micro-computer or a micro-processor and/or an electronic or electric circuit, preferably programmable, which is going to transmit the printing instructions to the head but also control the means or the hydraulic elements of the system for supplying with ink and with solvent, notably the pumps with solvent and/or ink and/or the valves of the system, in particular the valve 60, in order to manage the supply of the circuit with ink and/or with solvent as well as the recovery of the mixture of ink and solvent from the head.

This controller or these control means can also collect the items of information of pressure or differences in pressure supplied by the sensors 26, 56, potential items of information of temperature, and calculate or estimate the flow rate and/or the viscosity of the ink. It is also possible to carry out one or several offset corrections, as explained above. This controller or these control means can also:

command the sending of solvent, in order to adapt the viscosity of the ink in the circuit, command a pump for pressurising the ink, in order to adapt the flow rate of the latter.

The controller or the control means are thus programmed depending on the functions that have to be managed in the printer.

A device according to the invention may be incorporated in a system for controlling or servo-controlling at least one operating parameter of an ink jet printer. Compared to one or several set points of this (or these) parameter(s), for example flow rate and/or viscosity, a device according to the invention makes it possible to calculate or estimate one or several differences, which may be corrected or reduced using means for controlling or servo-controlling this (or these) parameter(s).

More particularly, the combination of an umbilical and pressure sensors 26, 56 as described above makes it possible to realise 2 controls or servo-controls:

a) a control or servo-control of the speed of the jets. For a multi-jet printer, the overall flow rate of the jets is used as control parameter, one and/or the other of the sensors 26, 56 may thus form the sensor(s) of a flow rate control loop; preferably the sensor 56 is used, the head playing the role of flow meter and the umbilical that of viscometer, b) a control or servo-control of the ink quality. It is possible to control or servo-control the ink concentration, or viscosity. The use of 2 sensors and the umbilical makes it possible to know the viscosity of the ink (as well as the overall flow rate of the jets).

A device as described above may be implemented in control or servo-control system according to the invention, forming one or several control loops implemented in a multi-jet printer.

The data provided by the sensors 26, 56 are linked: knowledge of the viscosity enables the flow meter to be precise and knowledge of the flow rate makes it possible, through the operating pressure, to determine correctly the viscosity of the fluid.

The two control loops are thus linked.

Preferably, the control or servo-control of the flow rate is priority, with a typical response time of the order of a second: the time difference between a modification of a parameter of the circuit (for example the speed of a pump) to modify the flow rate and the actual modification of the flow rate of the jets is less than or equal to 1 s. The management of ink quality through the control or servo-control of the viscosity is less priority and less rapid, a response time of the order of a minute being sufficient: the time difference between a modification of a parameter of the circuit (for example the opening of a valve for supplying with solvent) to modify the viscosity and the actual modification of the viscosity of the ink of the jets is around 1 min, or less than or equal to 1 min, or comprised between 30 s and 2 min.

Figure 5:
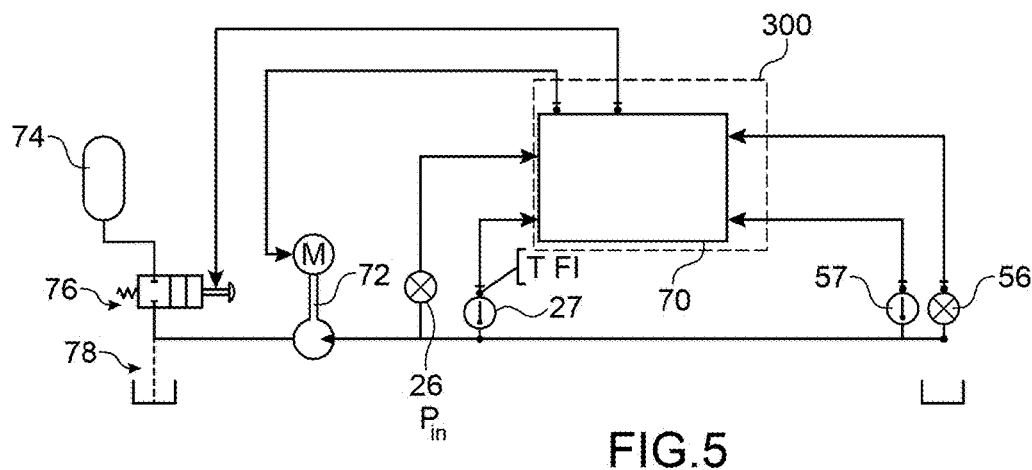
FIG. 5 is an exemplary embodiment of a flow rate and/or viscosity control or servo-control system according to the invention, for an ink jet printer.

As illustrated in FIG. 5, a central computer 70 (for example the controller of the printing machine) may be used to ensure these controls. This may form part of the controller or control means, in the body 300 of the printer.

The data in the memory of the computer may be the following:

a) The hydraulic characteristics of the umbilical 200: β$_0$, b) The hydraulic characteristics αHead and βHead of the head, c) The characteristics ρ and μ of the ink, for example measured in the laboratory.

The input data of the computer may be the following:

a) The pressure difference (Pin–PHead), supplied by the sensors 26, 56, b) The temperature Tin of the ink in, or near to, the sensor 56, 26 (measured using the temperature sensor 27, potentially integrated with one of the pressure sensors), c) The operating pressure P Head, provided by the sensor 56, d) The temperature of the ink in the head (T Head, measured using the temperature sensor 57, potentially integrated with the pressure sensor 56), e) A flow rate set point (which may be constant); this set point may be stored in a memory of the computer 70, f) A viscosity set point of the ink, which may be temperature dependent; this set point may also be stored in a memory of the computer 70.

The output data of the computer 70 are for example:

a) data for controlling the motor of a pump 72 for pressurising the ink circuit, with a view to a variation in the speed of this motor, b) and/or data for commanding an electromagnetic valve 76, with a view to addition of solvent into the circuit, from a solvent cartridge 140, for example via a circuit in part identical to the circuit for sending ink to the head.

With the memorised data and the input data, the computer 70 may (for example with the calculations already explained above) estimate or calculate the flow rate (or the speed) and/or the viscosity of the ink. The pressure data are preferably corrected for their offset.

For the control of the flow rate, a proportional type control or servo-control is suited. It is possible to take into account an integral term. The gain, which makes it possible to transform the difference in flow rate observed into difference in speed of the motor of the pump 72, may for example be obtained by measurements carried out on a representative set of machines. It is preferable to give greater importance to the precision than to the rapidity of the servo-control by choosing a gain not having a risk of servo-control pumping (rapidity is often a source of exceeding the target value, a system that reacts rapidly being able to find itself below the latter and to do so on several occasions; this is known as "pumping").

For the control of the viscosity, a proportional-integral type control or servo-control is suited. From the practical point of view, the gain in the control or servo-control (proportional term and integral term) may be obtained in an experimental manner.

The addition of a derived term (expressing the trend to deviate from the set point: either one approaches the set point or the target value and the trend or the slope is negative, or one moves away from the set point or target value and the trend or the slope is positive) is possible, but of limited interest. In fact, an advantage of this measurement system, giving viscosity and flow rate, is to benefit from a continuous (or practically continuous) measurement of the viscosity, for example with a difference of a second (or more) between 2 consecutive measurements. The fact of benefiting from a continuous, or very frequent, measurement, makes it possible:

to modulate and adapt a volume of solvent to add, to control or servo-control from filtered or averaged viscosity values; in fact, in a CIJ printer equipped with a flow time measurement viscometer, a viscosity measurement value is only available around every 8 minutes and it is possible to ensure correct control or servo-control of ink quality. By having available a measurement value frequently, for example each second, it is possible to treat the measured values (for example by calculation of an average, and/or by filtering, etc.), by means for calculating an average or by a filter.

to be able to monitor the effects of additions of solvent on a printer having a quicker response time than a CIJ type printer. In fact the response time of a printer is mainly associated (all other things being equal) with the transfer time of the ink from the ink reservoir (in which it is stored) to the print head (in the places where the effects of the viscosity of the ink are visible). A simple calculation makes it possible to evaluate the ratio of the response times between a binary multi-jet type printer and a CIJ printer (single jet or twin jet).

For example, by making the following hypotheses:

identical lengths of umbilical between the two types of printers, inner diameter of the pressure pipe of a binary multi-jet type printer: 2.7 mm; inner diameter of the pressure pipe of a CIJ type printer: 1.6 mm, flow rate of the jets for a binary multi-jet type printer 3.1 l/h; flow rate for a CIJ type printer: 0.24 l/h, On the basis of these hypotheses, this gives a ratio of the response time (binary multi-jet/CIJ)=$(1.6/2.7)^2 \times 3.1/0.24 = 4.5$.

It is possible to verify experimentally the response of the flow rate and viscosity controls or servo-controls:

1) to an instantaneous difference, that is to say the response to a scale interval, for example to a difference of 10% compared to a so-called nominal flow rate value, 2) and/or to a viscosity difference, for example a difference of 1 Centipoise, 3) and/or to a temperature ramp, for example comprised between 0° C. and 50° C. with a slope of 5° C./h.

A measurement of the flow rate or speed of the jets and/or viscosity according to the invention, and potentially a control or servo-control of the pressure and/or the viscosity as explained above, may be carried out during printing of a multi-jet ink jet printer.

Figure 6:
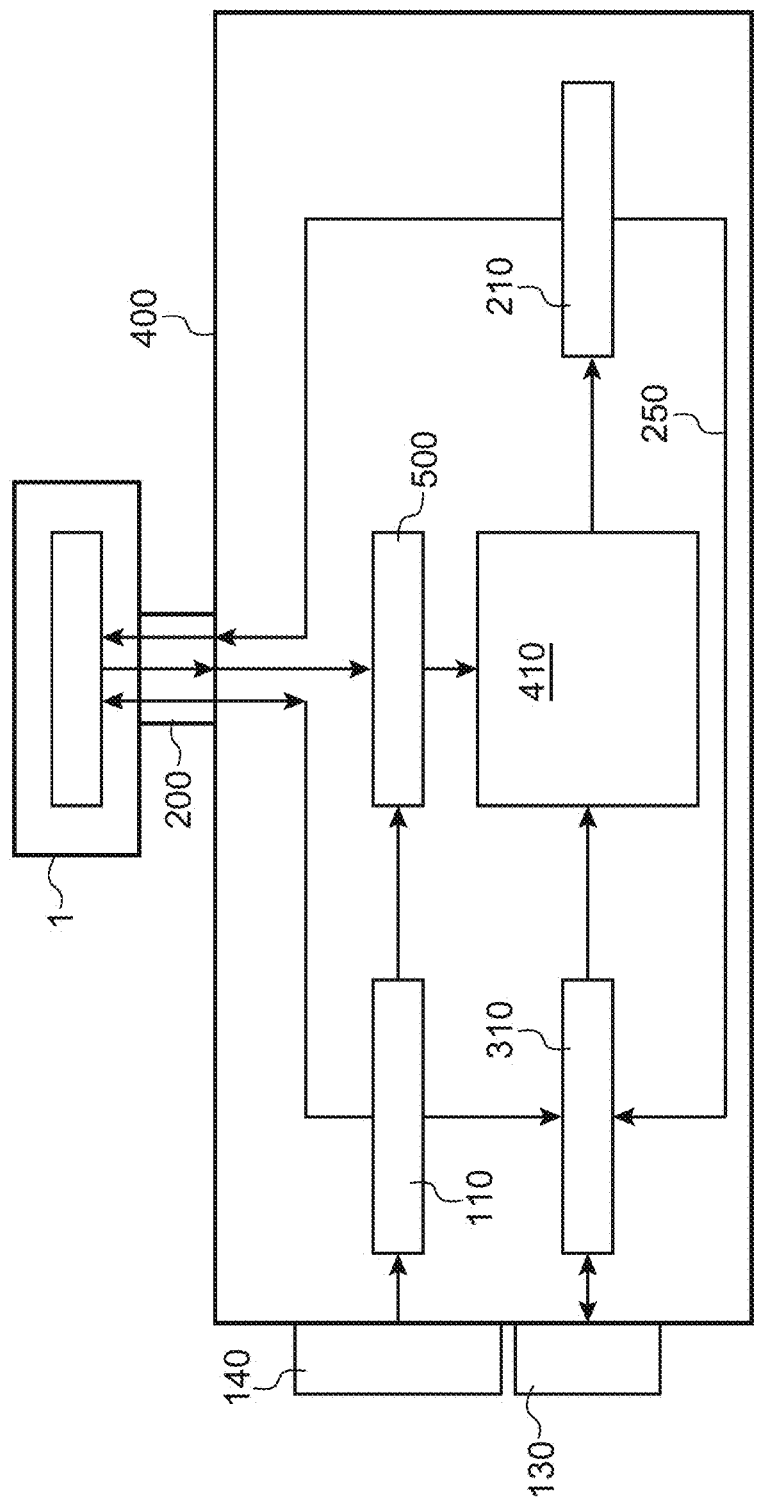
FIG. 6 represents an example of fluidic circuit structure to which the invention may be applied.

What has been described above, for example the system described in relation with FIG. 5, may be applied to an example of architecture of the fluidic circuit of a printer as illustrated in FIG. 6.

An example of architecture of the fluidic circuit of a printer to which the various aspects of the invention may be applied, individually or in combination, is illustrated in FIG. 6. References identical to those already used previously designate identical or corresponding elements. In particular, there is again the flexible umbilical 200, which groups together the hydraulic and electrical connections and the print head 1, to which the printer architecture described below may be connected.

In this FIG. 6, it may be seen that the fluidic circuit 400 of the printer comprises a plurality of means 410, 500, 110, 210, 310, each associated with a specific functionality.

With this circuit 400 are associated a removable ink cartridge 130 and a solvent cartridge 140, also removable.

The reference 410 designates the main reservoir, which makes it possible to collect a mixture of solvent and ink.

The reference 110 designates the set of means that make it possible to withdraw, and potentially to store, solvent from a solvent cartridge 140 and to supply the solvent thus withdrawn to other parts of the printer, whether it involves supplying the main reservoir 410 with solvent, or cleaning or maintaining one or more of the other parts of the machine.

The reference 310 designates the set of means that make it possible to withdraw ink from an ink cartridge 130 and to provide the ink thus withdrawn to supply the main reservoir 410. As may be seen in this figure, according to the embodiment described here, the sending, to the main reservoir 410 and from the means 110, of solvent, goes through these same means 310.

At the outlet of the reservoir 410, a set of means, globally designated by the reference 210, makes it possible to pressurise the ink withdrawn from the main reservoir, and to send it to the print head 1. According to one embodiment, illustrated here by the arrow 250, it is also possible, by these means 210, to send ink to the means 310, then once again to the reservoir 410, which enables a recirculation of the ink inside the circuit. This circuit 210 also makes it possible to empty the reservoir in the cartridge 130 and to clean the connections of the cartridge 130

The system represented in this figure also comprises means 500 for recovering fluids (ink and/or solvent) which return from the print head, more exactly the gutter 7 of the print head (FIG. 2) or the circuit for rinsing the head. These means 500 are thus arranged downstream of the umbilical 200 (with respect to the direction of circulation of the fluids that return from the print head).

As may be seen in FIG. 6, the means 110 may also make it possible to send solvent directly to these means 500, without going through either the umbilical 200 or through the print head 1 or through the recovery gutter.

The means 110 may comprise at least 3 parallel supplies of solvent, one to the head 1, the $2^{nd}$ to the means 500 and the $3^{rd}$ to the means 310.

Each of the means described above is provided with means, such as valves, preferably electromagnetic valves, which make it possible to orient the fluid concerned to the chosen destination. Thus, from the means 110, it is possible to send exclusively solvent to the head 1, or to the means 500 or to the means 310.

Each of the means 500, 110, 210, 310 described above is provided with a pump that makes it possible to treat the fluid concerned (respectively: $1^{st}$ pump, $2^{nd}$ pump, $3^{rd}$ pump, $4^{th}$ pump). These different pumps ensure different functions (those of their respective means) and are thus different to each other, even if these different pumps may be of same or similar type: none of these pumps ensures 2 of these functions).

In particular, the means 500 comprise a pump ($1^{st}$ pump) which makes it possible to pump the fluid, recovered, as explained above, from the print head, and to send it to the main reservoir 410. This pump is dedicated to the recovery of this fluid coming from the print head and is physically different to the $4^{th}$ pump of the means 310 dedicated to the transfer of ink or the $3^{rd}$ pump of the means 210 dedicated to the pressurisation of ink at the outlet of the reservoir 410.

The means 110 comprise a pump (the $2^{nd}$ pump) which makes it possible to pump solvent and to send it to the means 500 and/or to the means 310 and/or to the print head 1. It is for example the pump 72 of FIG. 5.

A device according to the invention, notably of the type described in relation with FIG. 6, comprises for example the structure described above in relation with FIG. 3. Possible means for a control or servo-control of such a device have been described above, in particular in relation with FIG. 5.

A structure of a print head that can be implemented within the scope of the invention has been described above in relation with FIG. 2 and mainly comprises:
- a drop generator 1;
- means, or sorting unit, 6 which make it possible to separate drops intended for printing from drops or sections of jets that do not serve for printing;
- a gutter 7 for recovering drops or sections of jets that do not serve for printing.

According to one embodiment, the drop generator comprises one or more stimulation chambers, each chamber being associated with a nozzle.

For example, on the nozzle plate 2 (FIG. 2) are aligned, along an X axis, a whole number n of nozzles 4, of which a first $4_1$ and a last nozzle $4_n$.

The first and last nozzles ($4_1$, $4n$) are the nozzles the furthest away from each other.

Figure 7A:
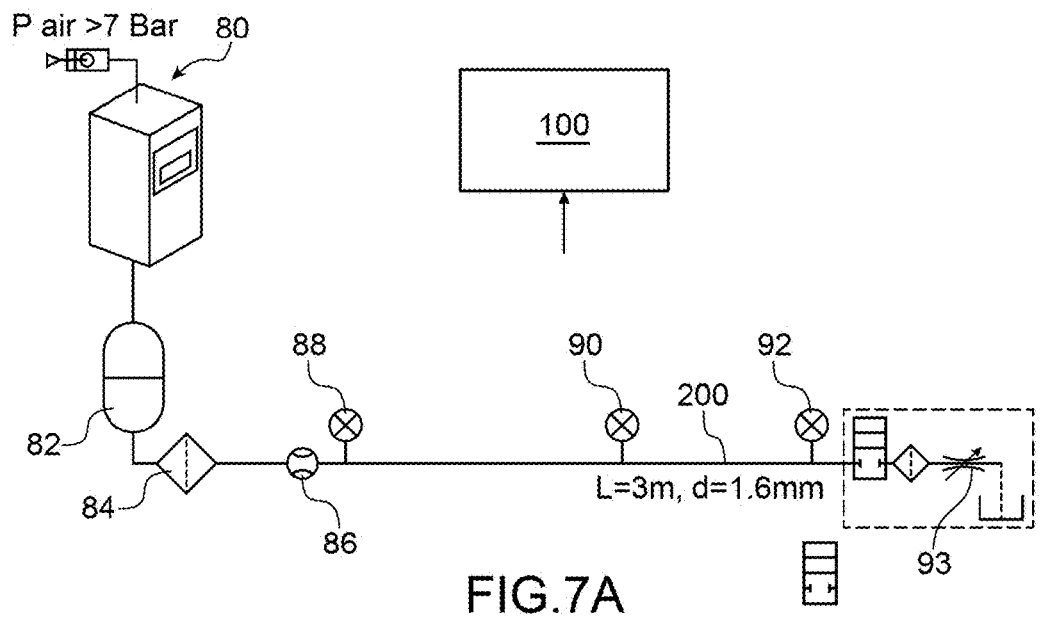
FIGS. 7A and 7B represent examples of device for measuring one or several hydraulic coefficients in a device according to the invention.
Figure 7B:
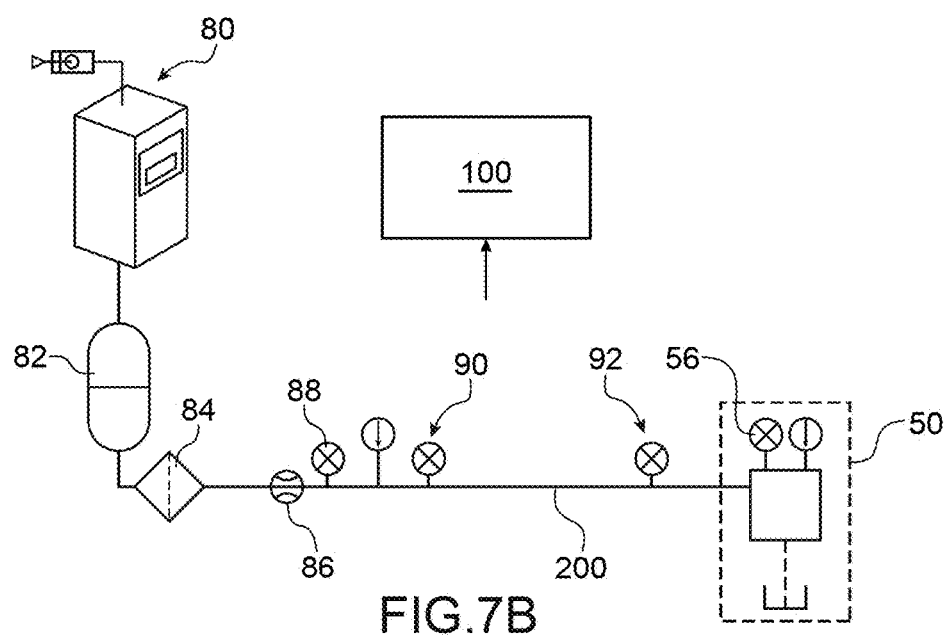

To determine the coefficients $\beta_0$ or $\alpha$Head, $\beta$Head, for example at the moment of production of the printers, it is possible to use a mounting such as that illustrated in FIG. 7A or 7B, which comprises an assembly for generating a precisely regulated pressurised fluid. This assembly comprises a reserve 82 of fluid pressurised by compressed air using a pressure regulator 80, preferably electrically commanded, to impose a regulated pressure in the circuit, for example at least 4 bars from a pressure source of at least 7 bars (preferably the pressure difference between the pressure source and the regulated pressure is at least 1 bar to obtain a well-regulated pressure). The electrically commanded pressure regulator 80 makes it possible, from a voltage value, to obtain a pressure that is maintained constant in the reservoir 82. This assembly supplies a filter 84, a precision flow rate sensor 86, a pressure sensor 88. The element to test, and of which it is wished to determine the parameters $\alpha$ and/or $\beta$, is here the umbilical 200. A calibrated orifice 93 simulates the operation of the head. The sensor 88 is a reference pressure sensor. It makes it possible to verify, by coherence, that the other sensors equipping the device and/or the print head do not supply aberrant values.

In the case of a measurement of the parameters $\alpha$Head and $\beta$Head of a print head 50 (FIG. 7B), this replaces the calibrated orifice 93, as illustrated in FIG. 7B.

In a variant, the system of FIG. 7A could characterise both the 2 components (umbilical 200 and head 50) by maintaining the umbilical 200 in place and by replacing the orifice 93 by the print head 50. By equipping a printing machine with a precision flow meter (such as that noted 80 in FIG. 7A or 7B) and a precision sensor (such as that noted 88) it is possible to obtain all the necessary items of information. The advantage of such a system is that the test bench is the machine itself (easy to duplicate and to transport and which can be used throughout the world, etc.

In both cases, the use of a Coriolis type flow meter 86 has the advantage of enabling very precise measurement of the flow rate, the temperature and the specific gravity (or density, for example in kg/m$^3$) of the fluid.

The viscosity measurement may be carried out simply by withdrawal of fluid then measurement in the laboratory on a Couette type viscometer (of which the precision is satisfactory). In a variant, it is possible to measure the viscosity using 2 pressure sensors 90 and 92 arranged as indicated in FIGS. 7A and 7B, at the ends of the umbilical 200. The pressure difference between these 2 sensors provides information directly on the viscosity of the fluid (a first calibration makes it possible to determine the relation between head loss and viscosity (calibration of the viscometer) then the viscosity is obtained from the pressure difference between 90 and 92). Advantageously, a calibration (correspondence curve) between the measurement (Pin-Pout) and the measurement of viscosity in the laboratory makes it possible to obtain the viscosity measurement directly, without other in-line measurements (thus without measurement of the pressure, the specific gravity (or density, for example in kg/m$^3$), the temperature, or the flow rate).

It is this mounting that has made it possible to verify the hypothesis of relation between pressure loss, viscosity and flow rate:

$$Pin-PHead=\beta_0 \times \mu \times q$$

The principle of the characterisation device of FIG. 7A is the following. For a given calibrated orifice 93 (here 0.28 mm), the regulated pressure of the fluid reserve is made to vary from a zero value to a maximum value (close to 6 bars).

The flow rate circulating in the element to characterise (here: the umbilical) varies from a zero value (or practically zero) to a maximum value.

A data acquisition system makes it possible to obtain simultaneously all of the items of information given by the element to characterise and enabling the calculation of the hydraulic coefficients ($\alpha$, $\beta$, as already explained above).

Figure 8:
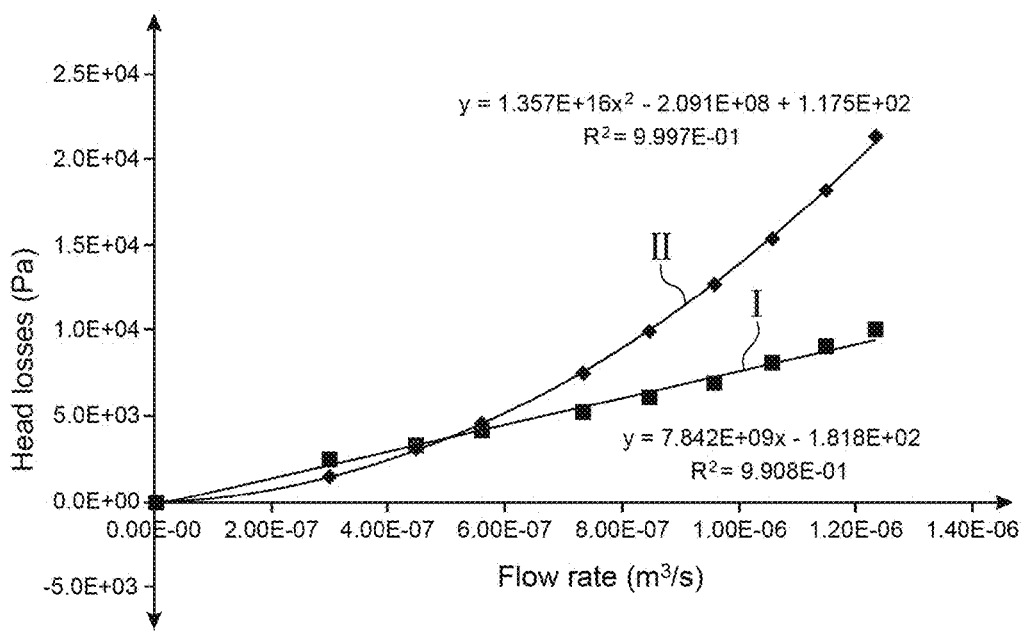
FIG. 8 represents curves of head loss as a function of flow rate in a device according to the invention.

Examples of results are given in FIG. 8.

For the umbilical, the curve l (x term) is exploited to know the regular head loss coefficient of the umbilical.

For the simulation of the head (with singular and regular head losses): the curve II is exploited to know the singular ($x^2$ term) and regular (x term) head loss coefficients.

The squares of the correlation coefficients are given in this figure and clearly show that the correlations are greater than 99%.

It may be observed that the offset compensations are carried out correctly (the curves pass very close to the origin).

A device as illustrated in FIG. 7A or 7B makes it possible to collect data that are going to make it possible to link, on the one hand, the pressure difference, (Pin−PHead)/q and, on the other hand, the flow rate q, and finally to obtain the coefficients ($\alpha$, $\beta$).

In a variant to what has been described above, the device of FIG. 7B may be used in the following manner.

It may be observed that, from equations (1), (2) or (1'), (2') above, the following relation may be established (PHead being measured at the outlet of the umbilical):

$$\alpha Head \cdot q^2 = (PHead - (\beta Head/\beta_0)(Pin - PHead))/\rho$$

If the second term of this equality is constant, then the jet flow rate is constant.

The following tests may thus be carried out, assuming the temperature ($T_0$), viscosity ($\mu_0$), and density ($\rho_0$) values are constant.

An upper flow rate (qsup) and a lower flow rate (qinf) are chosen, the "target" flow rate q (3.1 l/h in the example) being comprised between these two values. For example qsup=3.32 l/h (for an average speed of the jets of 15 m/s), qinf=2.88 l/h (for an average speed of the jets of 13 m/s).

Then, the following are measured:
for the flow rate qinf: PHeadinf and Pininf,
for the flow rate qsup: PHeadsup and Pinsup.

From these measured values and the equations that have already been given above, it is possible to calculate the values of $\alpha$Head, $\beta$Head and $\alpha_0$.

It may then be verified that:
the calculated value of PHead (for q=3.1 l/m (target value) in the above example) indeed gives the measured flow rate (3.1 l/h in the example) it is thus verified here that the calculated value of Phead for the target flow rate indeed generates this target flow rate,
the head loss of the umbilical is coherent with the calculations.

If the verification is coherent with expectations, then the following values of A and B may be retained, which may notably be used for the flow rate and viscosity control or servo-control:

for the control or servo-control of the flow rate:
A=(PHead−($\beta$Head/$\alpha_0$) (Pin−P Head)) ($\alpha$Head, $\beta$Head and $\beta_0$ may be obtained and verified according to the principles described above and the values PHead and (Pin−PHead) are measured during the verification of the target flow rate; in fact all the values making it possible to calculate A are obtained during the step of calculation and verification of the characteristics $\alpha$Head, $\beta$Head and $\beta$0) and the value of the specific gravity (or density, for example in kg/m$^3$) of the ink ($\rho_0$); the pressure control or servo-control then aims to regulate PHead so as to keep constant: A×$\rho$(T)/$\rho_0$, for the control or servo-control of viscosity:
B=(Pin−PHead) (measured or estimated according to the same principles as those described above for A) and the value of the viscosity of the ink ($\mu_0$); the viscosity control or servo-control then aims to regulate the additions of solvent so as to maintain constant: (Pin−PHead)/B=$\mu$(T)/$\mu_0$.

In yet a further variant to what has been described above, the device of FIG. 7B may be used in the following manner.

It is possible to establish the characteristics $\alpha$Head, $\beta$Head and $\beta_0$ by studying the response of the system to a flow rate ramp.

For example, in a period of time, preferably reduced, the flow rate is made to go from a minimum value, called lower flow rate (qinf) to a maximum value, called upper flow rate (qsup). The target value of the flow rate qjet is preferably situated very close to the average of qinf and qsup.

The change in pressures over the duration ($t_{end}-t_0$) of the flow rate ramp is recorded.

For example, the flow rate goes from qinf=2.6 l/h to qsup=3.6 l/h in 60 seconds.

It is thus possible, assuming constant the temperature ($T_0$), viscosity ($\mu_0$), and density ($\rho_0$) values, to measure Pin, P Head and q at $t_0$ and $t_{end}$ (respectively start and end of the flow rate ramp).

It is then possible to plot as a function of time:
a first curve which gives (Pin−P Head)/$\mu_0$×q(t); this curve is practically a horizontal line, the average value of which gives $\beta_0$,
a second curve which gives (PHead)/q(t); by applying a linear regression to these curves, an intercept b and a slope a are obtained; b/$\mu_0$=$\beta$Head and a/$\rho_0$=$\alpha$Head.

It may also be noted that, generally speaking, if $\beta_0$ is available, it is possible to obtain the viscosity $\mu$ by plotting Pin−P Head as a function of q.

A data acquisition system 100 makes it possible to collect all the items of information necessary for the calculations of the hydraulic coefficients ($\beta_0$ or $\alpha$Head, $\beta$Head).

This system 100 comprises for example a micro-computer or a micro-processor and/or an electronic or electric circuit, preferably programmable, which is going to collect the items of information of flow rate or pressure or pressure differences supplied by the sensors 86, 88, 90, 92, the potential items of information of temperature, and calculate or estimate (Pin−PHead), q, and the coefficients ($\beta_0$ and/or $\alpha$Head, $\beta$Head). Advantageously, this system 100 also manages the pressure regulator 80, the reserve 82; the result is thus an automated system for characterising components.

During printing on a support 800, a flow rate and/or viscosity measurement may be carried out using a device according to the invention; a correction of the flow rate and/or the viscosity may be implemented during printing. It is thus possible to carry out measurements as soon as the jets are established, the fact of printing or not printing does not change the flow rate of the jets at the level of the nozzles.

The precision of the system such as that of FIG. 3 has been characterised with the following characteristics:

the print head comprises 64 nozzles, each of a diameter of 35 µm, the nominal speed of the drops is 14 m/s, the umbilical has a length of 3 m and an inner diameter of 2.7 mm, The real values of the characteristics of the fluid and the jet are the following:

$\rho_0$=850 kg/m³;

$\mu_0$=4.5 cps;

q=3.102 l/h;

αHead=0.1500;

βHead=159.80;

β0=6.392;

PHead=3457.3 mbars;

Pin=3546.5 mbars.

The measured values of the characteristics of the fluid and the jet are the following, the values in "Δ" indicating the absolute uncertainty, the values in brackets indicating the relative uncertainty on the measurement of the corresponding value:

$\rho_{prod}$=854. 25 kg/m³, $\Delta\rho_{prod}$=4.25 kg/m³ (0.5%);

$\mu_{prod}$=4.59 cps, $\Delta\mu_{prod}$=0.09 cps (2.0%);

The values of qsup (respectively qinf) are measured for a flow rate value equal to the value q mentioned above increased (respectively decreased) by 10% then affected by an error of 0.2% (the values in "Δ" indicating the absolute uncertainty, the values in brackets indicating the relative uncertainty):

qsup=3.419; Δqsup=0.006824 (0.2%);

inf=2.797; Δqinf=0.005583 (0.2%);

The following values of Pheadsup (respectively Pheadinf) result from the application of the formula (2') already mentioned above, by applying to it the above real values (but with, respectively, qsup and inf for the flow rate) and an error of 1%:

Pheadsup=3988.3 mbars;

Pheadinf=3039.2 mbars;

The head losses in the umbilical (that is to say the pressure difference between Pin and PHead) have been calculated with application of the formula (1') already mentioned above, by applying to it the above real values (but with, respectively, qsup and inf for the flow rate) and an error of 0.5%:

(Pin-PHead)sup 98.635

(Pin-PHead)inf=0.80.701

From the values measured above, the following are deduced:

αHeadcalculated=0.1507;

βHeadcalculated=158.24;

β0calculated=6.286;

Hence a difference, between values that result from measurement and those that result from real values:

ΔαHead=0.5%;

ΔβHead=−0.98%;

Δβ0=−1.67%;

According to a first calculation, the error compared to a pressure set point resulting from a flow rate set point (here: set point of 3.102 l/h) is measured: By applying the formulas (1') and (2') given above, with αHeadcalculated, βHeadcalculated, β0calculated and the real values above for the other parameters, errors are deduced on the flow rate of the jet, respectively on the viscosity, of −1.07%, respectively +1.11% (absolute values of −0.033 l/h, respectively 0.050 cps).

According to a second calculation (using $q^2$=(PHead−(βHead/β_0) (Pout−PHead))/αHead·ρ and Pout−P Head=β_0×µ×q), the error is estimated compared to a real flow rate of 3.102 l and a real viscosity of 4.5 Centipoise. Another calculation method gives errors on the flow rate of the jet, respectively on the viscosity, of −0.08%, respectively 2.12% (absolute values of 0.002 l/h, respectively 0.096 cps).

These errors result from taking into account all the accumulated errors and show the performances of a system according to the invention.

The invention claimed is:

1. Print head of an ink jet printer and device for measuring the flow rate and the viscosity of ink sent to the print head, comprising:

a conduit, for supplying said print head, this conduit being provided with a $1^{st}$ pressure (Pin) sensor at a first end and a $2^{nd}$ pressure (PHead) sensor at a $2^{nd}$ end, this $2^{nd}$ pressure (PHead) sensor being situated in the print head, a circuit or a controller for measuring at least the pressure (PHead) of the $2^{nd}$ pressure sensor and the pressure difference (Pin−PHead) between the $1^{st}$ pressure sensor and the $2^{nd}$ pressure sensor.

2. Print head of an ink jet printer and device for measuring the flow rate and the viscosity of ink sent to the head, according to claim 1, said circuit or controller being capable of calculating the flow rate and the viscosity of the ink as a function of the pressure (PHead) of the $2^{nd}$ pressure sensor and the pressure difference (Pin−PHead).

3. Print head of an ink jet printer and device for measuring the flow rate and the viscosity of ink sent to the head, according to claim 2, the circuit or the controller being capable of calculating the flow rate and the viscosity of the ink as a function of the hydraulic characteristics (αHead, βHead) of the print head, the regular head loss coefficient (β_0) of said conduit, the specific gravity (ρ) of the ink, the pressure difference (Pin−PHead) and the pressure (Pin).

4. Print head of an ink jet printer and device for measuring the flow rate and the viscosity of ink sent to the head, according to claim 1, comprising said circuit or said controller being capable of correcting a measurement difference, for at least one same pressure, between the $1^{st}$ pressure sensor and the $2^{nd}$ pressure sensor and/or a sensitivity error of at least one of the pressure sensors.

5. Print head of an ink jet printer and device for measuring the flow rate and the viscosity of ink sent to the head, according to claim 4, the measurement difference, for at least one pressure, between the $1^{st}$ pressure sensor and the $2^{nd}$ pressure sensor, being corrected as a function of temperature.

6. Print head of an ink jet printer and device for measuring the flow rate and the viscosity of ink sent to the head, according to claim 1, said circuit or said controller being capable of correcting a measurement difference, for at least one pressure, between a pressure value measured by the $2^{nd}$ pressure sensor and said actual or real pressure.

7. Print head of an ink jet printer and device for measuring the flow rate and the viscosity of ink sent to the head, according to claim 6, the measurement difference, for at least one same pressure between a pressure value measured by the $2^{nd}$ pressure sensor and said actual pressure, being corrected as a function of temperature.

8. Print head of an ink jet printer and device for measuring the flow rate and the viscosity of ink sent to the head, according to claim 1, at least one of the 1$^{st}$ pressure sensor and 2$^{nd}$ pressure sensor being a flush membrane pressure sensor with a flat membrane situated at one end of the 2$^{nd}$ pressure sensor, the flat membrane being flush with the measured flow.

9. Print head of an ink jet printer and device for measuring the flow rate and the viscosity of ink sent to the head, according to claim 1, said print head being a multi-jet print head.

10. Print head of an ink jet printer and device for measuring the flow rate and the viscosity of ink sent to the head, according to claim 1, said circuit or said controller being capable of controlling or correcting the pressure and/or the viscosity of the ink supplied as a function of the measurements of the flow rate and the viscosity of the ink.

11. Ink jet printer comprising:
a print head and a device for measuring the flow rate and the viscosity of ink sent to the print head, according to claim 1,
a hydraulic circuit for forming a flow of fluid to send to said print head.

12. Method of printing using an ink jet printer, comprising a measurement of the flow rate and/or the viscosity of the ink sent to a print head of an ink jet printer and its device for measuring the flow rate and the viscosity of ink sent to the head according to claim 1.

13. Method of printing using of an ink jet printer, according to claim 12, further comprising a step of measuring the flow rate and/or the viscosity of the ink and a step of correcting the flow rate and/or the viscosity of the ink.

14. Print head of an ink jet printer and device for measuring the flow rate and the viscosity of ink sent to the print head, comprising:
a conduit, for supplying said print head, this conduit being provided with a 1$^{st}$ pressure (Pin) sensor at a first end and a 2$^{nd}$ pressure (PHead) sensor at a 2$^{nd}$ end, this 2$^{nd}$ pressure (PHead) sensor being situated in the print head,
means for measuring at least the pressure (PHead) of the 2$^{nd}$ pressure sensor and the pressure difference (Pin−PHead) between the 1$^{st}$ pressure sensor and the 2$^{nd}$ pressure sensor.

15. Print head of an ink jet printer and device for measuring the flow rate and the viscosity of ink sent to the head, according to claim 14, further comprising means or a circuit or a controller for calculating the flow rate and the viscosity of the ink as a function of the pressure (PHead) of the 2$^{nd}$ pressure sensor and the pressure difference (Pin−PHead).

16. Print head of an ink jet printer and device for measuring the flow rate and the viscosity of ink sent to the head, according to claim 15, said means or circuit or controller being capable of calculating the flow rate and the viscosity of the ink as a function of the hydraulic characteristics ($\alpha$Head, $\beta$Head) of the print head, the regular head loss coefficient ($\beta_0$) of said conduit, the specific gravity ($\rho$) of the ink, the pressure difference (Pin−PHead) and the pressure (Pin).

17. Print head of an ink jet printer and device for measuring the flow rate and the viscosity of ink sent to the head, according to claim 14, comprising means or a circuit or a controller, for correcting, preferably as a function of temperature, a measurement difference, for at least one same pressure, between the 1$^{st}$ pressure sensor and the 2$^{nd}$ pressure sensor and/or a sensitivity error of at least one of the pressure sensors.

18. Print head of an ink jet printer and device for measuring the flow rate and the viscosity of ink sent to the head, according to claim 14, comprising means or a circuit or a controller for correcting, preferably as a function of temperature, a measurement difference, for at least one pressure, between a pressure value measured by the 2$^{nd}$ pressure sensor and said actual or real pressure.

19. Print head of an ink jet printer and device for measuring the flow rate and the viscosity of ink sent to the head, according to claim 14, further comprising means or a circuit or a controller for controlling or correcting the pressure and/or the viscosity of the ink supplied as a function of the measurements of the flow rate and the viscosity of the ink.

20. Ink jet printer comprising:
a print head and a device for measuring the flow rate and the viscosity of ink sent to the print head, according to claim 14,
a hydraulic circuit for forming a flow of fluid to send to said print head.

* * * * *